United States Patent
Olsen et al.

(10) Patent No.: US 11,269,028 B2
(45) Date of Patent: Mar. 8, 2022

(54) SYSTEM AND METHOD FOR REAL-TIME INTERVENTIONAL DEVICE LOCALIZATION USING MAGNETIC RESONANCE IMAGING

(71) Applicant: Wisconsin Alumni Research Foundation, Madison, WI (US)

(72) Inventors: Miles E. Olsen, Madison, WI (US); Ethan K. Brodsky, Madison, WI (US); Walter F. Block, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 854 days.

(21) Appl. No.: 14/725,847

(22) Filed: May 29, 2015

(65) Prior Publication Data
US 2016/0349335 A1  Dec. 1, 2016

(51) Int. Cl.
*G01R 33/28* (2006.01)
*A61B 34/10* (2016.01)
(Continued)

(52) U.S. Cl.
CPC ............ *G01R 33/287* (2013.01); *A61B 10/02* (2013.01); *A61B 17/3403* (2013.01);
(Continued)

(58) Field of Classification Search
CPC .................................................. G10R 33/287
See application file for complete search history.

(56) References Cited

U.S. PATENT DOCUMENTS 6,195,577 B1  2/2001  Truwit et al.
6,782,288 B2  8/2004  Truwit et al.
(Continued)

FOREIGN PATENT DOCUMENTS

EP       1958588 A2      8/2008
WO   WO-2004104611 A2 * 12/2004  ........... G01R 33/287

OTHER PUBLICATIONS

Brodsky, et al., Intraoperative Device Targeting Using Real-Time MRI, Biomedical Sciences and Engineering Conference (BSEC), 2011, IEEE, pp. 1-4.
(Continued)

*Primary Examiner* — Rochelle D Turchen
(74) *Attorney, Agent, or Firm* — Quarles & Brady LLP

(57) ABSTRACT

A system and methods are provided for controlling interventional devices using magnetic resonance imaging ("MRI") guidance. In some aspects, the method includes arranging a pivoting guide about a subject's anatomy that is configured to direct an interventional device toward a selected target point within the subject's anatomy, generating, using an MRI system, MR data associated with markers placed on the pivoting guide, and determining a vector defining an orientation of the pivoting guide from locations for the markers identified using the MR data. The method also includes orienting the pivoting guide in multiple directions to determine multiple vectors, and identifying a pivot point for the pivoting guide using the determined vectors. The method further includes determining a trajectory for the interventional device using the identified pivot point and the selected target point, and controlling the interventional device along the determined trajectory.

14 Claims, 12 Drawing Sheets

(51) Int. Cl.
*A61B 10/02* (2006.01)
*A61B 90/11* (2016.01)
*A61B 17/34* (2006.01)
*G01R 33/48* (2006.01)
*A61B 90/00* (2016.01)

(52) U.S. Cl.
CPC .............. *A61B 34/10* (2016.02); *A61B 90/11* (2016.02); *G01R 33/286* (2013.01); *A61B 2090/374* (2016.02); *A61B 2090/3954* (2016.02); *G01R 33/4824* (2013.01)

(56) References Cited

U.S. PATENT DOCUMENTS

| | | | | |
|---|---|---|---|---|
| 6,853,191 | B1* | 2/2005 | Miller | G01R 33/56509 |
| | | | | 324/307 |
| 2005/0054913 | A1* | 3/2005 | Duerk | G01R 33/287 |
| | | | | 600/423 |
| 2006/0079754 | A1* | 4/2006 | Welch | G01R 33/4824 |
| | | | | 600/410 |
| 2009/0131783 | A1 | 5/2009 | Jenkins et al. | |
| 2011/0137156 | A1* | 6/2011 | Razzaque | A61B 18/1477 |
| | | | | 600/424 |
| 2013/0154640 | A1* | 6/2013 | Block | G01R 33/48 |
| | | | | 324/309 |
| 2013/0231554 | A1* | 9/2013 | Jung | G01R 33/56366 |
| | | | | 600/419 |

OTHER PUBLICATIONS

Larson, et al., An Optimized System for Interventional MRI Guided Stereotactic Surgery: Preliminary Evaluation of Targeting Accuracy, Neurosurgery, 2012, 70(Operative):ons95-ons103.
Martin, et al., Minimally Invasive Precision Brain Access Using Prospective Stereotaxy and a Trajectory Guide, Journal of Magnetic Resonance Imaging, 2008, 27:737-743.
Pintilie, et al., Visualization Platform for Real-Time, MRI-Guided Cardiac Interventions, Proc. Intl. Soc. Mag. Reson. Med., 2011, 19:3735.
Santos, et al., Flexible Real-Time Magnetic Resonance Imaging Framework, Engineering in Medicine and Biology Society, 2004, IEMBS'04, 26th Annual International Conference of the IEEE, vol. 1, pp. 1048-1051.
Smith, et al., Novel Circumferential Immobilization of Breast Tissue Displacement During MR-Guided Procedures: Initial Results, Proc. Intl. Soc. Mag. Reson. Med., 2008, 16:1212.
Truwit, et al., Prospective Stereotaxy: A Novel Method of Trajectory Alignment Using Real-Time Image Guidance, Journal of Magnetic Resonance Imaging, 2001, 13:452-457.
Weib, et al., Projection-Reconstruction Reduces FOV Imaging, Magnetic Resonance Imaging, 1999, 17(4):517-525.
PCT International Search Report and Written Opinion, PCT/US2016/034667, dated Sep. 7, 2016.

* cited by examiner

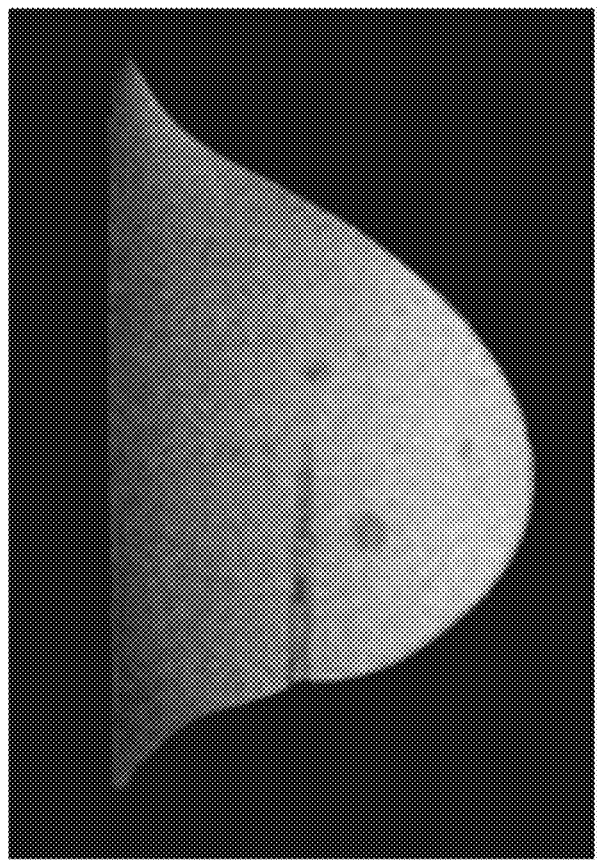
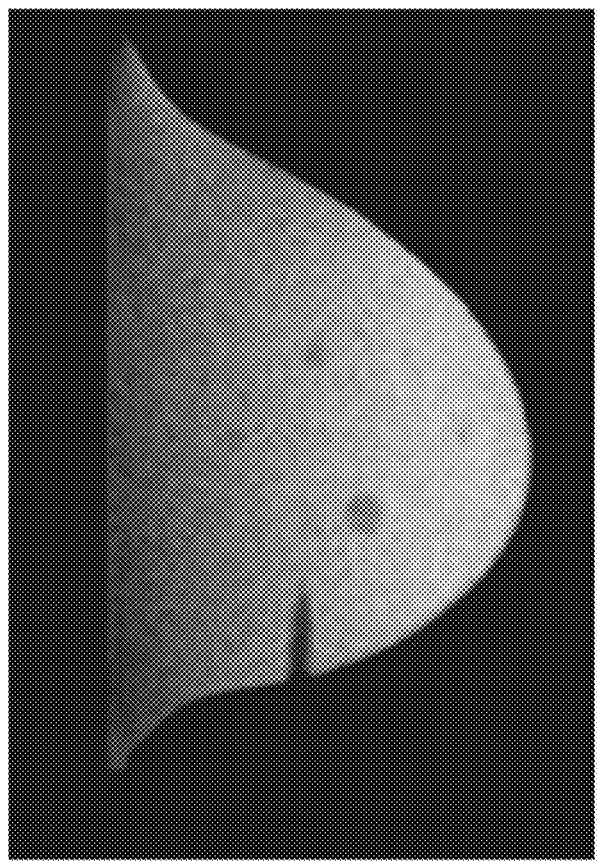
FIG. 8

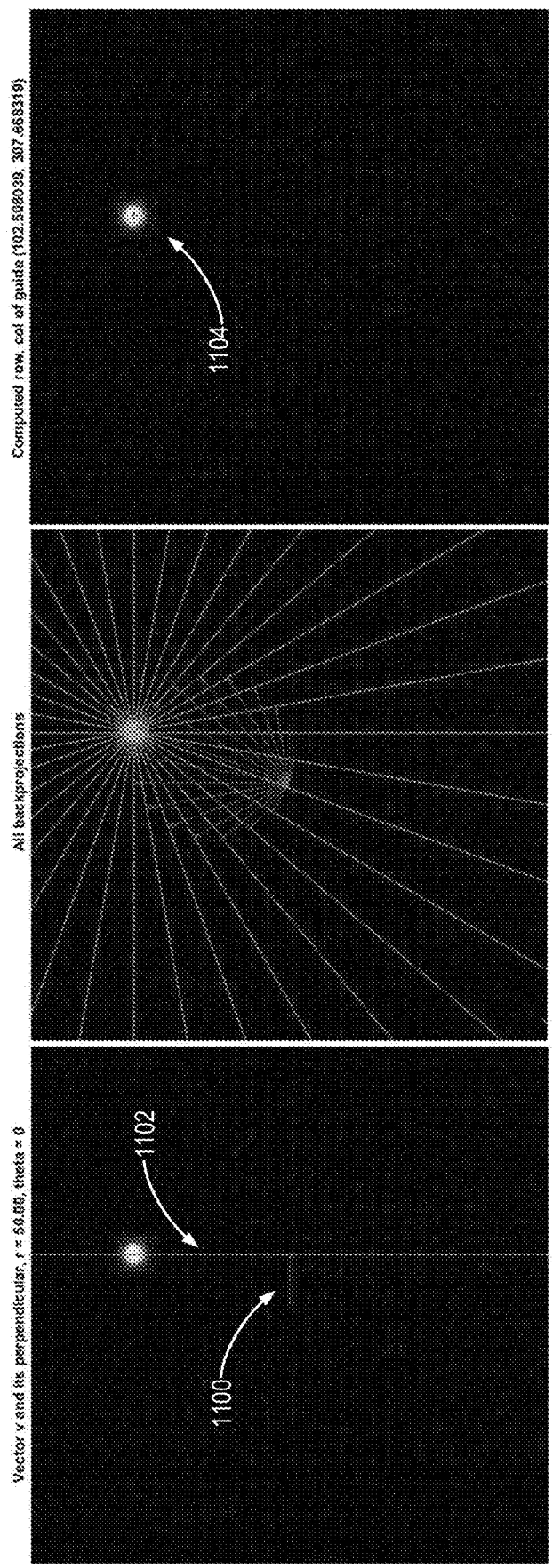

SYSTEM AND METHOD FOR REAL-TIME INTERVENTIONAL DEVICE LOCALIZATION USING MAGNETIC RESONANCE IMAGING

STATEMENT REGARDING FEDERALLY SPONSORED RESEARCH

This invention was made with government support under MH100031 awarded by the National Institutes of Health. The government has certain rights in the invention.

BACKGROUND

The present disclosure relates to systems and methods for interventional or intra-operative medical procedures. More particularly, the present disclosure is directed to systems, devices and methods for localizing interventional tools or devices using image guidance.

At present, many invasive procedures, such as neurosurgeries or breast biopsies, involve inserting a rigid device into the body using stereotactic image guidance. Traditionally, image guidance can be performed using retrospective of analysis of pre-operative images, such as x-ray or magnetic resonance ("MW") images, acquired during a planning stage that is performed in advance of the invasive procedure. However, the stereotactic coordinates of some tissue structures may change from the planning stage, and hence a lack of intra-operative imaging can complicate efforts to precisely target such structures during the procedure. As some image guidance tasks require sub-millimeter accuracy, methods for orienting devices that avoid the limitations of human error are desirable.

With respect to interventions in the brain, some functional approaches have been developed. For example, one approach to functional neurosurgery relies upon conventional three-dimensional MR images to produce a brain "roadmap" with good gray/white matter contrast. In order to gain access to the brain, a brain port, which includes a movable alignment guide that is visible on MR images, is attached to the skull over a craniotomy location. Additional images are then acquired to determine proper alignment of the guide, and the device is inserted therethrough and into the target anatomy. For instance, the device may be a hollow cannula for pumping a liquid agent or relieving a brain fluid.

In order to properly aim such an alignment guide, one simple method has included identifying a target point in the subject's anatomy and a pivot point for the guide, as described in U.S. Pat. Nos. 6,195,577 and 6,782,288. These points then define a 3D line representing an insertion trajectory. Two-dimensional imaging planes orthogonal to the trajectory are then acquired to view the guide's cross section and determine how the aim must be adjusted so that the guide is pointing along the trajectory. However, while geometrically simple, the above approach relies on the interventionist's ability to interpret images during the procedure, including visually locating the pivot point of the guide.

Some devices employ more complex ports that include orientable and translatable stages. However, such devices are much heavier, costlier, and more complex to use than less-complex brain ports. In addition, operation of these devices requires longer processes that include iterative scanning and adjustment, which is time-consuming and unintuitive to surgeons. Moreover, instead of running the operation, a surgeon is often required to defer portions of such procedures to a team of technologists and physicists.

Given the above, there remains a need for systems and methods that facilitate high-precision device placement in an intuitive, efficient, manner.

SUMMARY

The present disclosure provides systems and methods that overcome the aforementioned drawbacks by guiding an interventional device placement using magnetic resonance imaging ("MRI"). Specifically, systems and methods are provided that significantly improve upon previous technologies for device alignment and monitoring during specific medical procedures, such as functional neurosurgery or breast biopsy. In particular, previous reliance upon image interpretation and longer, iterative imaging steps can be replaced by computational measurement, and interactive real-time tuning. That is, the present disclosure provides systems and methods implementing an approach that provides a clinician with rapid, visual feedback that affords intuitive, real-time device manipulation. In addition, the approach described lends itself to full or a high level of automation, such that minimal or no operator input is required.

In one aspect of the disclosure, a method for controlling an interventional device using magnetic resonance imaging ("MRI") guidance is provided. The method includes arranging a pivoting guide about a subject's anatomy, the pivoting guide configured to direct an interventional device toward a selected target point within the subject's anatomy, generating, using an MRI system, MR data associated with at least a first marker placed on the pivoting guide, and a second marker, longitudinally displaced from the first marker along the pivoting guide, and determining a vector defining an orientation of the pivoting guide from locations for the imaged first marker and second marker identified using the MR data. The method also includes orienting the pivoting guide in multiple directions and repeating above steps for each direction to determine multiple vectors. The method further includes computing a pivot point for the pivoting guide using the determined vectors, determining a trajectory for the interventional device using the identified pivot point and the selected target point, and controlling the interventional device along the determined trajectory.

In another aspect of the disclosure, a method is provided for controlling an interventional device using magnetic resonance imaging ("MRI") guidance. The method includes generating, using an MRI system, MR data of an interventional device arranged about a subject's anatomy and having a first marker and a second marker placed on the interventional device. The first marker and the second marker are separated in at least one axial direction of the interventional device. The method further includes determining locations for the first marker and the second marker relative to the subject's anatomy using the MR data, and computing a vector using the identified locations. The method also includes determining at least one of a location or an orientation for the interventional device relative to the subject's anatomy using the computed vector, projecting a future arrangement of the interventional device within the subject's anatomy using the determined location or orientation, and generating a report indicating the future arrangement of the interventional device relative to the location or orientation.

In yet another aspect of the disclosure, a system for controlling an interventional device using magnetic resonance imaging ("MRI") guidance is provided. The system includes an MRI system configured to image at least a portion of an interventional device comprising a pivoting guide. The system also includes a processor programmed to direct the MRI system to acquire data indicative of a first marker placed on the pivoting guide, and a second marker, longitudinally displaced from the first marker along the pivoting guide, and determine a vector defining an orientation of the pivoting guide from locations for the imaged first marker and second marker using the data. The processor is also configured to determine multiple vectors for each one of a number of orientations for the pivoting guide, and compute a pivot point for the pivoting guide using an intersection of the determined vectors. The processor is further configured to determine a trajectory for orienting the interventional device using the identified pivot point and a selected target point within a subject's anatomy, and generate a report indicative of the determined trajectory.

The foregoing and other aspects and advantages of the invention will appear from the following description. In the description, reference is made to the accompanying drawings that form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

FIG. 8 shows example Cartesian images acquired in real-time during a robotic insertion.

FIG. 11A is an image showing the determination of a vector and its perpendicular line determined from the correlation data of FIG. 10D.

FIG. 11B is an image showing the full set of lines determined from the multiple projections shown in FIG. 9B.

FIG. 11C is an image showing the determined guide stem center location obtained by computing the intersection of the lines of FIG. 11B.

DETAILED DESCRIPTION

Figure 1:
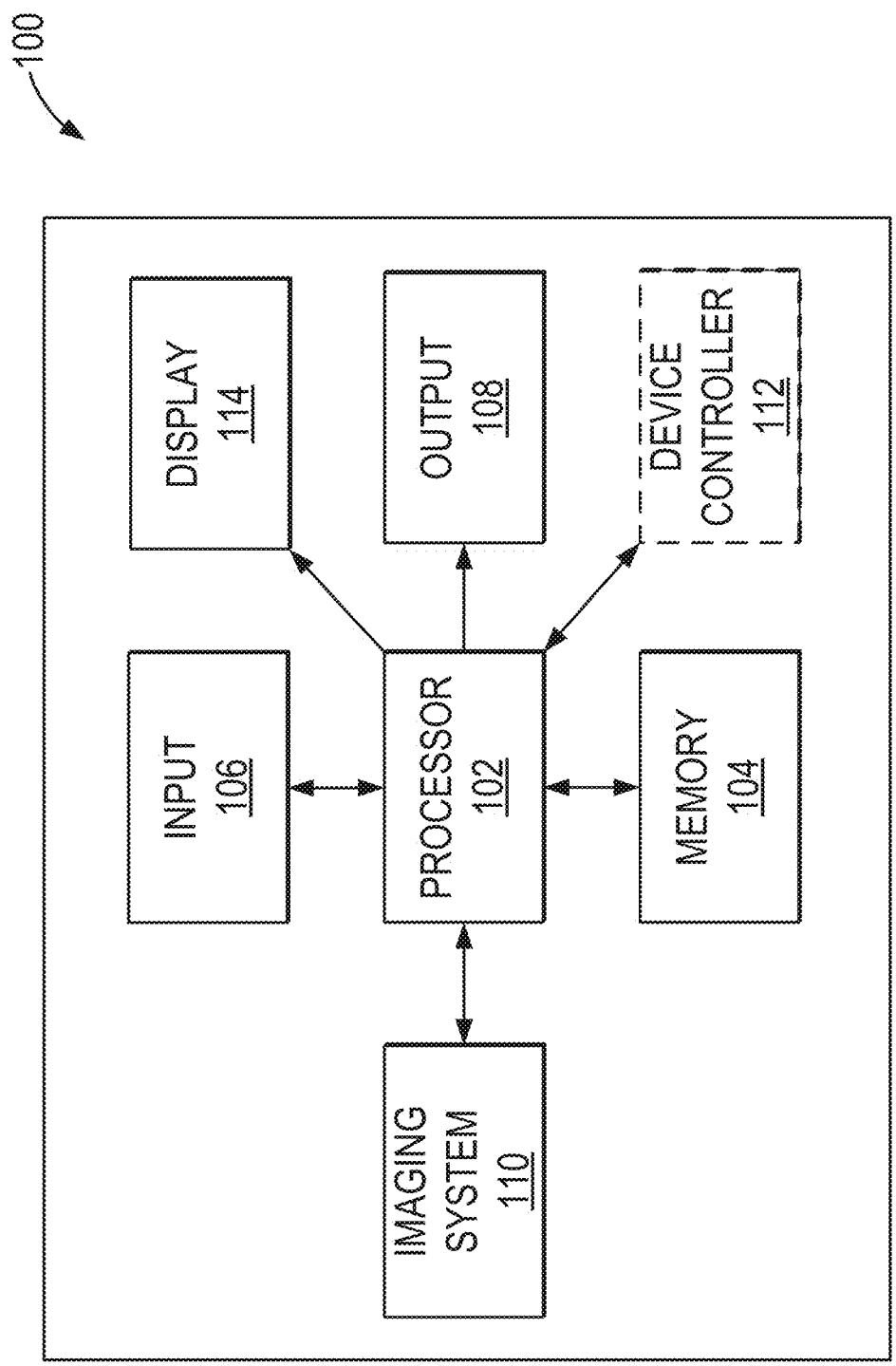
FIG. 1 is a block diagram for an example system in accordance with aspects of the present disclosure.

The present disclosure describes a system and methods for use in medical procedures that provide improved interventional device alignment and monitoring using image guidance. In general, previous approaches for guiding interventional devices have employed high-resolution three-dimensional ("3D") anatomical images, considered necessary for achieving a high placement accuracy. The field of view ("FOV") of the 3D anatomical images is enlarged to cover MR-visible features of the alignment device. The slow process of device alignment is performed by iteratively adjusting the device alignment and then 3D imaging the device and surrounding anatomy. The alignment is iteratively refined until the trajectory path of the inserted device meets a physician-selected target with an acceptable accuracy. As appreciated, such approach is slow and subject to error.

By contrast, the present disclosure describes an approach that rapidly captures positional information associated with an interventional device or device guide without need for human interpretation of images, nor time-consuming iterations involving imaging full anatomical features. Specifically, the present disclosure implements real-time magnetic resonance ("MW") data acquisition and analysis to quickly and accurately enable clinicians or surgeons to prepare and control an interventional device during a medical procedure. For instance, highly undersampled radial trajectories through k-space may be utilized to produce very accurate guidance cues that enable real-time manipulation and alignment of commercially available devices.

In some aspects, the system and methods described herein may be utilized to improve operation of a specific medical apparatus or device, such as a brain port, for example. In general, brain ports are utilized to provide a controlled access to a subject's brain, and include movable alignment guides with MR-visible fluid-filled cavities. To determine the correct aim of such an alignment guide, clinicians identify the pivot point of the guide by examining acquired images and looking for the proximal point where the fluid-filled cavity terminates. In practice, alignment guides are not always identical at this point, which makes it difficult for the clinicians to identify the true physical pivot point every time over the course of several procedures that may use different guides. Also, different brain ports may be used, which adds a further layer of potential complexity. Therefore, in accordance with aspects of the present disclosure, a system and method is provided that includes performing computational measurements of two or more marker positions along a pivoting guide, oriented in several directions, and allows the computation of vectors that can accurately determine a pivoting point, and identify the guide's current orientation in real-time.

As will be appreciated from descriptions herein, aspects of the present disclosure may be applied to neurosurgical interventional procedures, such as thermal ablation, for epilepsy and other lesion types, placement of deep brain stimulation electrodes, and managing tumor resection with fiber tracking for arteriovenous malformation and aneurysms, to name but a few clinical applications and interventional devices. Other applications may also include local delivery of cells or medications to specific anatomical locations, such as the brain, via manual or computer-controlled pump injection through an inserted cannula. In addition, the provided systems and methods may be applied to other interventional procedures, including biopsy procedures. However, it may be appreciated by one of ordinary skill in the art, that the present systems and methods may be utilized in other applications.

Turning to FIG. 1, a system 100 for controlling placement of an interventional device using imaging guidance is provided. In some configurations, the system 100 can include a processor 102, a memory 104, an input 106, an output 108, an imaging system 110, and an optional device controller 112, as shown in FIG. 1. However the system 100 may be any device, apparatus or system configured for carrying out instructions for or controlling an orientation or an insertion of an interventional device, and may operate as part of, or in collaboration with a computer, system, device, machine, mainframe, or server. For instance, in some configurations, the system 100 need not include the imaging system 110, and instead be configured to communicate with an external imaging system (not shown in FIG. 1). In this regard, the system 100 may be a system that is designed to integrate with a variety of software and hardware capabilities and functionalities and capable of operating autonomously. In some aspects, the system 100 may be portable, such as mobile device, or apparatus. In addition, in some configurations, the system 100 may also include or be used in cooperation with an interventional device or apparatus configured for carrying out a medical procedure, such as a biopsy, or a neurosurgery. In some aspects, the interventional device includes a pivoting guide, while in other aspects, the pivoting guide or other device guide having MR-visible markers, may be configured separately from the interventional device.

In addition to being configured to carry out a number of steps for the system 100 using instructions stored in the memory 104, the processor 102 may be configured to direct acquisition and processing of image data generated using an imaging system 110, such as an MRI system. In accordance with aspects of the present disclosure, the processor 102 may be programmed to implement a data acquisition using a fast MR imaging sequence, such as a gradient recalled echo sequence, to achieve real-time measurements. By way of example, the processor 102 may direct the MRI system to perform an undersampled radial k-space sampling sequence. It should be appreciated that other data acquisition strategies may also be implemented. The processor 102 may also be configured to process one ("1D"), two dimensional ("2D") or three-dimensional ("3D") image data acquired using the imaging system 110. Specifically, in accordance with aspects of the present disclosure, the processor 102 may be configured to analyze 1D projection data from within one or more 2D FOV planes, and identify signal patterns or features in the data, indicative of locations, shapes, dimensions, orientations, and other information, about objects within the FOV, preferably in real-time. For instance, the processor 102 may be configured to determine the locations, configurations of markers placed on an imaged interventional device or apparatus. The processor 102 may also be configured to determine and analyze the shape of the cross-section of the MR-visible markers. In some aspects, the processor 102 may utilize identified signal patterns or features to verify whether a selected device or apparatus is being utilized appropriately, or whether the correct device or apparatus is in use.

In some implementations, the processor 102 may be programmed to reconstruct images using image data acquired from one or more imaging planes, and utilize the reconstructed images to characterize the imaged objects, including determining their respective locations, orientations, shapes, dimensions and so forth. However, in other implementations, readout datasets acquired using an MRI system may be directly utilized by the processor 102 to characterize the objects in each respective FOV without explicit need for reconstructing images. This can be achieved by using knowledge of where in k-space the readouts came from, as well as other information, such as a known device diameter, for example.

Figures 9A, 9B:
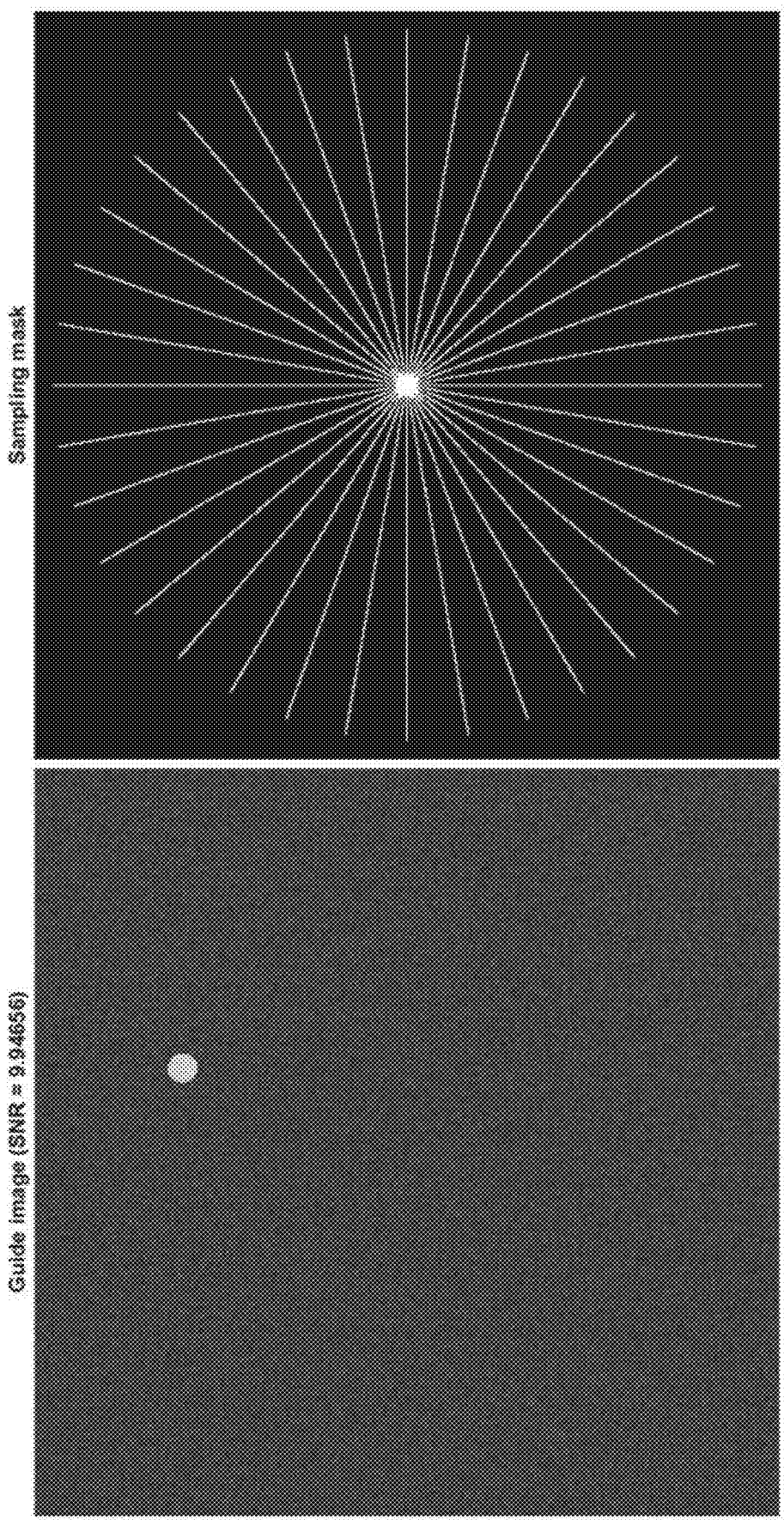
FIG. 9A shows an example synthetic image depicting the cross-section of an MR-visible guide stem.
FIG. 9B is an image associated with the image data of FIG. 9A showing where in k-space the projection readouts are sampled.
Figure 10A:
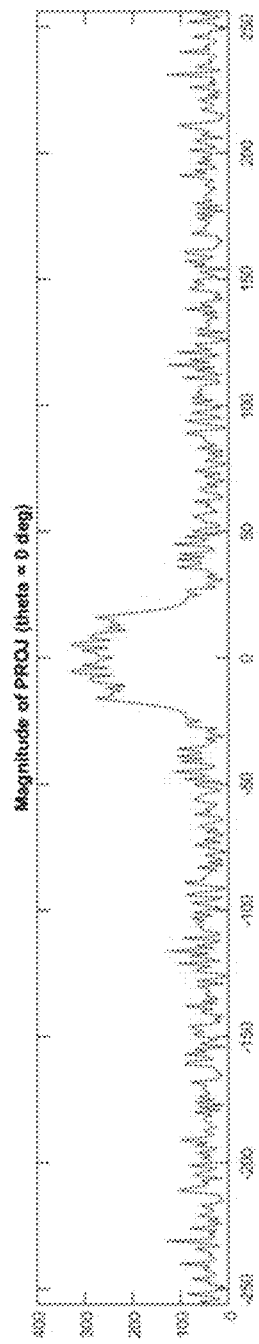
FIG. 10A is a graph showing the magnitude of an example projection readout derived from a single radial traversal of k-space.
Figure 10B:
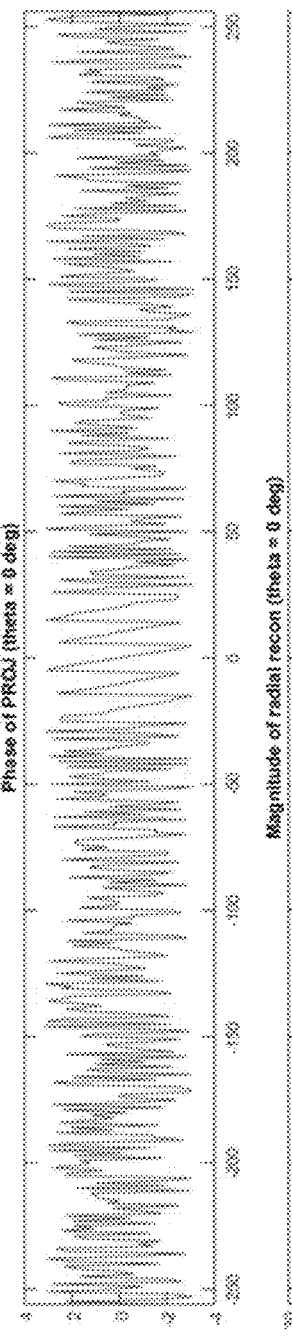
FIG. 10B is a graph showing the phase of the projection data of FIG. 10A.
Figure 10C:
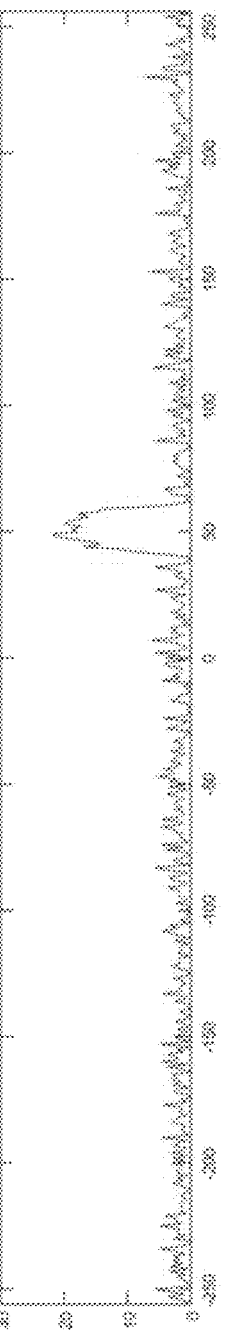
FIG. 10C is a graph showing the inverse Fourier transform of the projection readout data of FIGS. 10A and 10B.
Figure 10D:
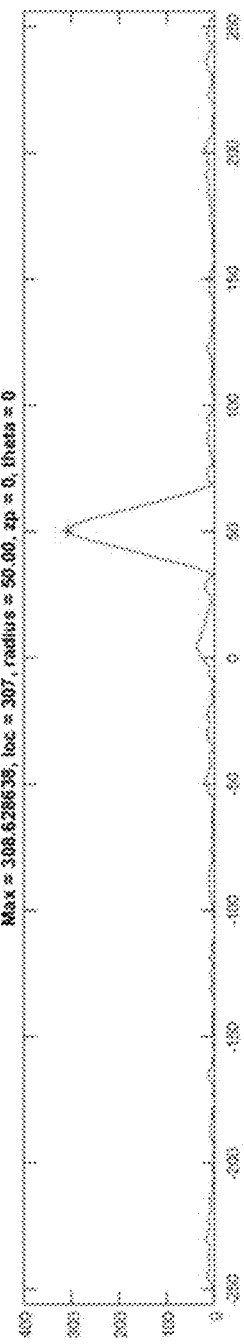
FIG. 10D is a graph showing the convolution of the data in FIG. 10C with a rectangular function of width equal to the device diameter.

To illustrate this point, FIG. 9A shows a synthetic image indicating a cross-section of an MR-visible guide stem with some added background noise. FIG. 9B shows the radial readouts in k-space, with the horizontal line corresponding to a readout angle of theta=0 degrees and the vertical line corresponding to theta=90 degrees. Considering an MR projection readout of 512 complex values for a given projection at theta=0 (depicted in FIGS. 10A and 10B as separate magnitude and phase components, respectively), a 1D inverse Fourier transform may be applied to produce a graph indicative of the location of the guide stem (FIG. 10C). Given the background noise, generally present in such datasets, a rectangular ("rect") function of similar width as the guide stem may be convolved with the 1D data sin image space (FIG. 10C). This process will produce large output values in regions that resemble the guide stem and small output otherwise. In fact, the convolution in image space is analogous to a multiplication in k-space. In some aspects, to make the computation simpler by avoiding a direct convolution, the readout data in k-space may be multiplied by the Fast Fourier Transform ("FFT") of the rect function, and then the 1D inverse FFT of that product may be computed to obtain the convolution in image space (FIG. 10D). This convolution smoothes the noise and produces clean peaks, indicative of the location of the guide stem. Effectively this is a cross-correlation between a 1D model of the guide and the noisy 1D reconstructed data in FIG. 10C, indicating the spatial shift between the field of view center the guide cross-section. In some aspects, the product in k-space may be zero padded to a greater length before applying the inverse FFT. This produces interpolated data points in the 1D convolution output in image space. This enables better determination of the peak location because, in general, the true peak center may not fall perfectly on one of the original (for instance, 512, in this case) sampled points.

FIG. 11A depicts the output of the dataset shown in FIG. 10D overlaid upon an eventually reconstructed 2D image. However, at this point in the data collection and processing, an image need not be formed. A vector 1100 shown in FIG. 11A is oriented along theta=0 degrees and has a length of 50 units, namely the radius at which the peak was found in the 1D convolution. A line 1102 perpendicular to the direction of the readout (namely the vector 1100) can then be constructed and stored. The line 1102 may be defined by a pair of 2D vectors, that is, one that indicates a point on the line 1102, and one that indicates the orientation of the line). The process can be repeated for all of the readouts (FIG. 9B), for example, as they are being acquired, as indicated in FIG.

11B. The guide stem center location 1104 can then be obtained by finding an approximate intersection of the stored lines, for example, using a linear least squares algorithm, such as a 2D linear least squares algorithm (shown in FIG. 11C).

Returning to FIG. 1, from the identified locations of the markers, a vector or line defining an orientation for the device may then be determined by the processor 102. In some aspects, markers placed on a pivoting guide, for use with an interventional device, for example, may be utilized to determine an orientation of the guide. In addition, a pivot point for the pivoting guide may also be determined by orienting the pivoting guide along multiple directions, and determining multiple vectors from the identified marker locations for each orientation. An intersection of the guide orientation vectors may then be computed by the processor 102 to determine the pivot point, for example, using a 3D linear least squares algorithm. Notably, the guide orientation vectors may not intersect perfectly at a single point. This may occur for a variety of reasons, such as the guide not extending in a perfect straight line, slight imprecision in the computation of the points that define the guide orientation vector, random noise in MRI signal, and the like. Thus, instead of using an analytical system of equations for computing the exact intersection point of lines, as will be described, a linear least squares algorithm may be used to find the point in 3-space, which minimizes the sum of the squared error, where the sum is over all guide orientation lines, and the error is the shortest distance between the point and a line defining an orientation. In any case, such a pivot point, along with a selected target point in the subject's anatomy provided via input 106, may be used by the processor 102 to determine a trajectory for aligning an interventional device.

In one non-limiting example, the processor 102 may communicate with a device controller 112 to control the position and orientation of the interventional device or pivoting guide. For instance, the processor 102 may provide instruction to the device controller 112 to position and/or orient the interventional device or pivoting guide along a determined or projected trajectory to a future position. The processor 102 may also coordinate movements of the interventional device or pivoting guide with imaging using the imaging system 110 to obtain images of the interventional device or pivoting guide in as it is moved to or toward a projected future position or orientation.

Alternatively, a clinician or operator may operate the interventional device or pivoting guide manually. As such, the processor 102 may be configured to direct the imaging system 110 to acquire and analyze image data, for example, in substantially real-time, and provide a report to the clinician or operator via output 108. In some aspects, the report may be provided via a display 114 and may include images of the interventional device or pivoting guide, as well as information related to identified signal patterns or features in the image data and/or images. In particular, the report may include real-time information regarding a location or orientation of an interventional device or pivoting guide, or markers placed thereupon. In some aspects, the report generated by the processor 102 may be in the form of an audio and/or visual signal configured to guide or indicate to the operator or clinician how to control the interventional device or pivoting guide to achieve a target position or orientation. For example, the report may indicate a future arrangement of the interventional device determined or projected by the processor 102 and be shown relative to current positions or orientations.

Figure 12A:
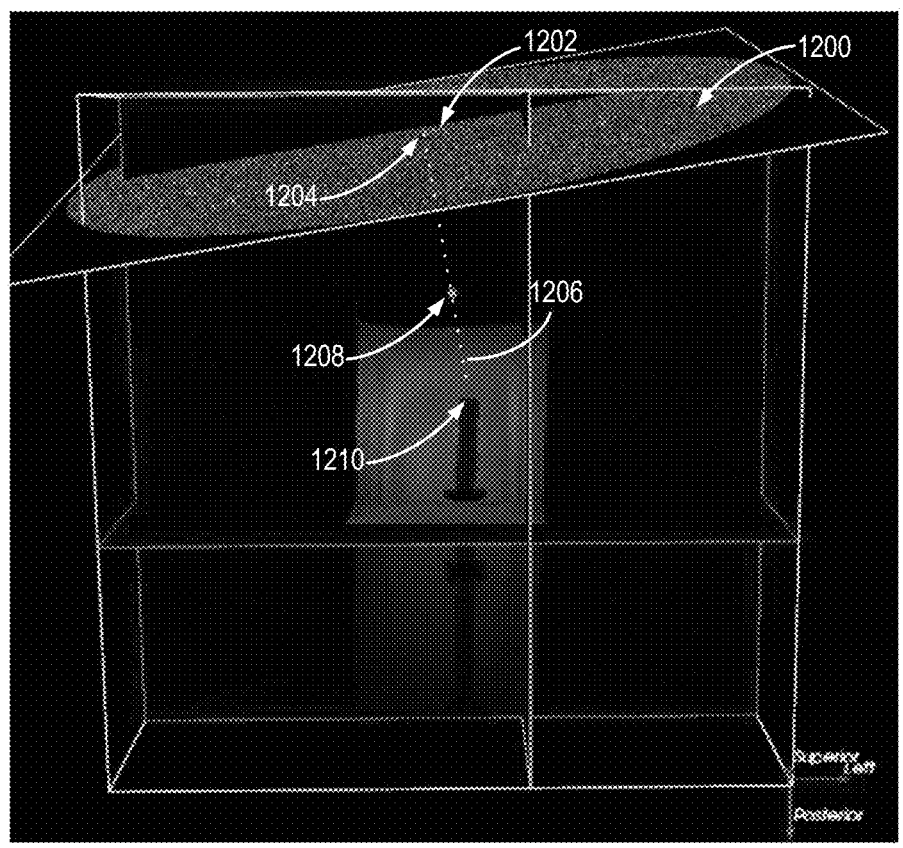
FIG. 12A shows an example 3D rendering depicting an imaging plane with a current marker position and a projected marker position computed using a trajectory determined from an identified pivot point and a selected target point.
Figure 12B:
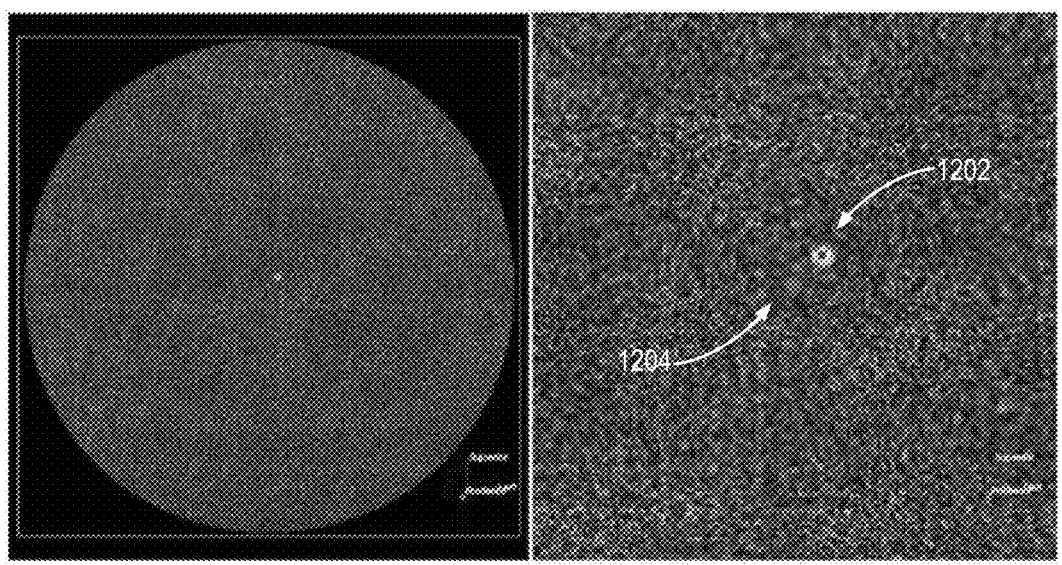
FIG. 12B shows an example 2D rendering depicting a current marker position and a projected marker position overlaid on a reconstructed 2D image.

By way of non-limiting example, FIG. 12A shows a 3D rendering depicting an imaging plane 1200 with a current marker position 1202 and a projected marker position 1204, which is computed using a trajectory 1206 determined from an identified pivot point 1208 and a selected target point 1210, as described. FIG. 12B shows the current marker position 1202 and the projected marker position 1204 overlaid on a reconstructed 2D image.

Figure 2:
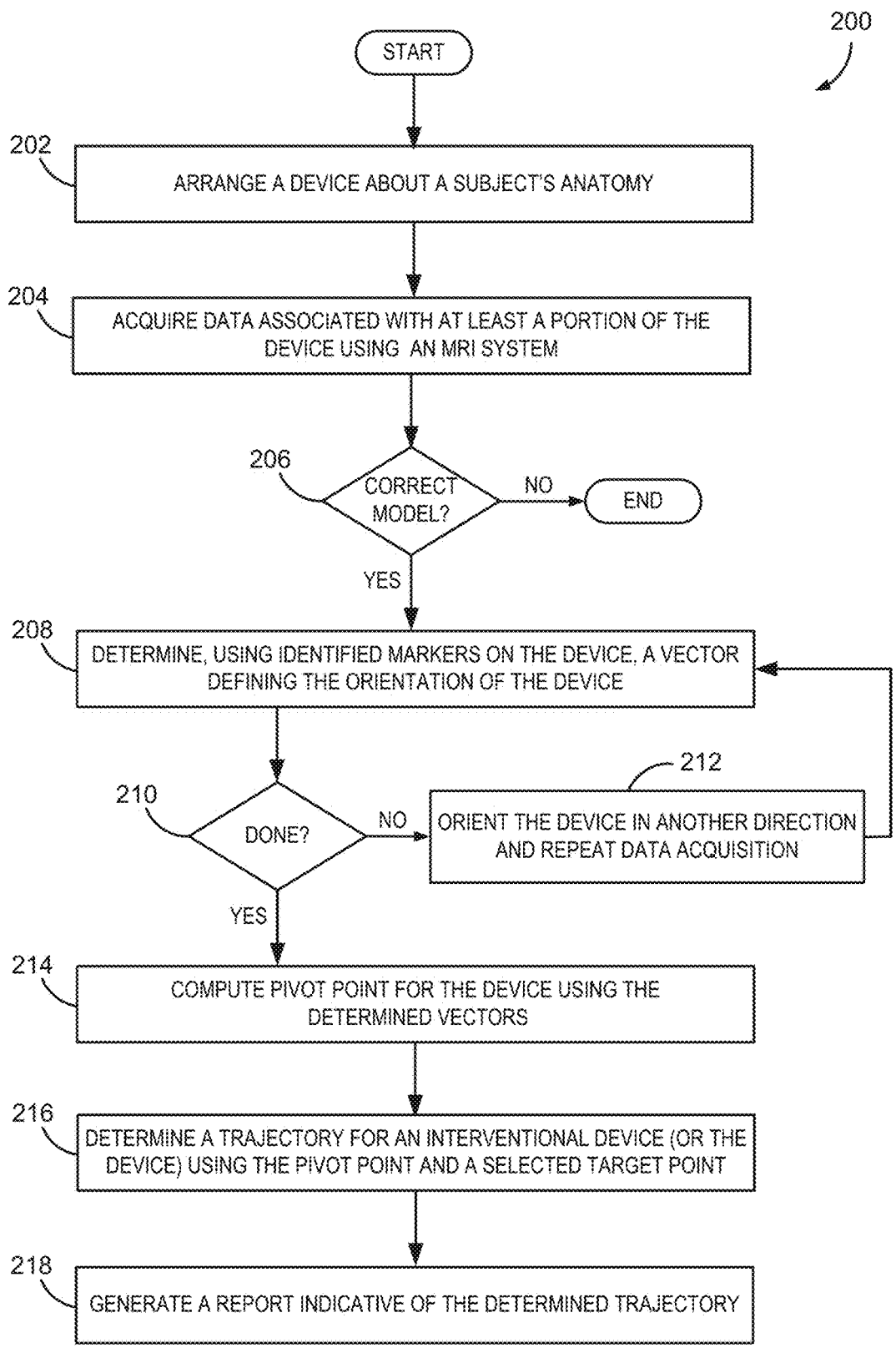
FIG. 2 is a flowchart setting forth steps of a process in accordance with aspects of the present disclosure.
Figure 3:
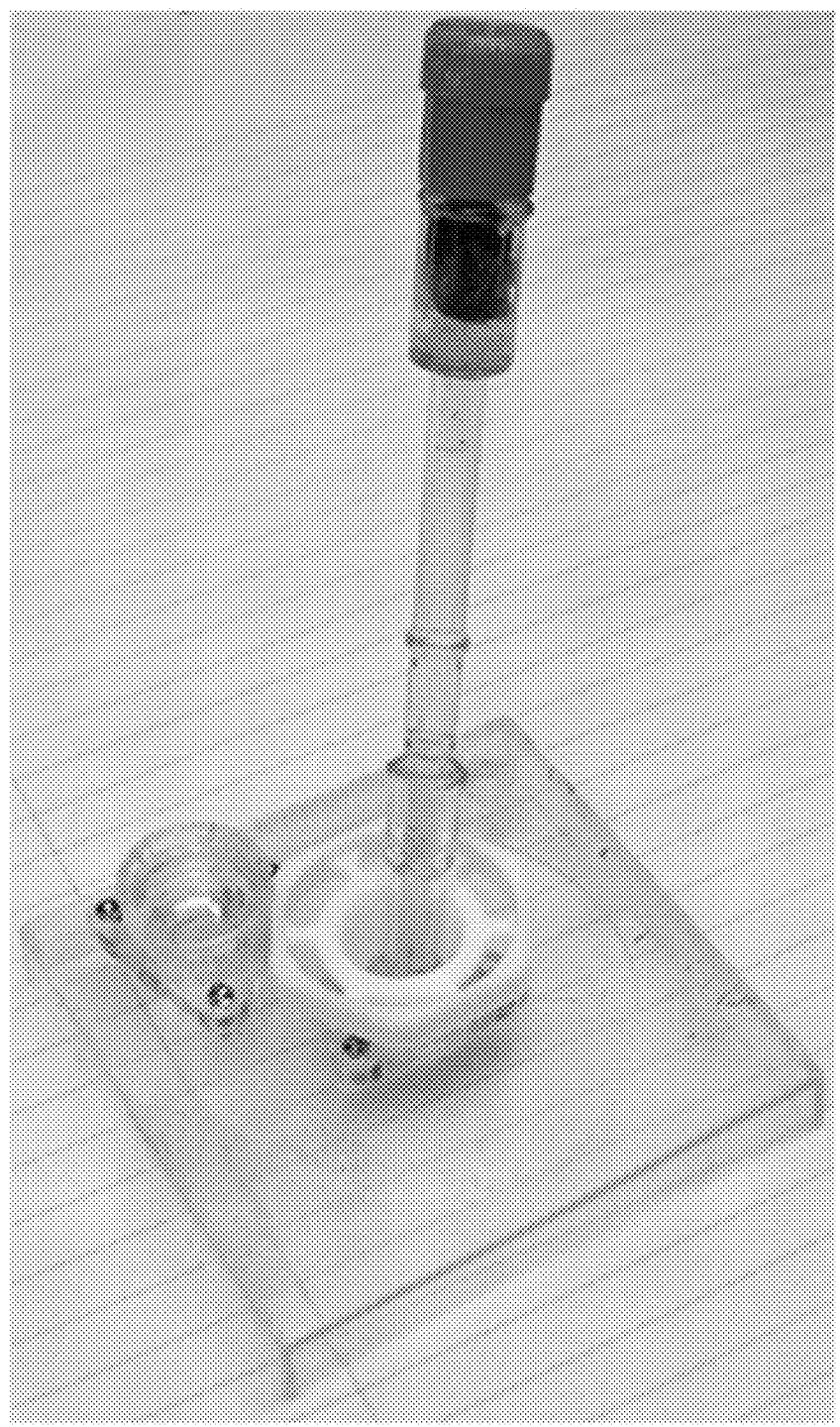
FIG. 3 is an example brain port that includes an alignment guide in a ball and socket joint.

Turning to FIG. 2, the steps of a process 200 for controlling an interventional device using image guidance, in accordance with aspects of the present disclosure, are shown. The process 200 may begin at process block 202 where a device, such as a pivoting guide or interventional device, is arranged about a subject's anatomy. As described, the device may be one used for any of a variety of applications, such as a brain port, as shown in the example of FIG. 3, and configured to movably direct an interventional device or apparatus, or component thereof, toward any selected target point or region within the subject's anatomy. In some aspects, the device may include a tube or lumen configured to receive a particular interventional device therethrough. For example, such an interventional device may include a trocar, or cannula, for example, for draining fluid from or inserting an agent into a portion of a subject's anatomy, or a device for obtaining a tissue biopsy.

In some aspects, imaging of a subject's anatomy may be acquired before or after execution of process block 202, in order to obtain anatomical information from the subject. For example, a detailed 3D image volume may be obtained in order to locate and select the target point or region for an intervention, biopsy, and so forth.

At process block 204, data associated with at least a portion of the device may be acquired using an imaging system, as described with respect to FIG. 1. In some implementations, data associated with multiple markers, longitudinally displaced along the device, may be acquired using an MRI system. For example, radial MR projection readout data may be acquired using the MRI system. In addition, an analysis of the image data and/or reconstructed images therefrom may also be performed at process block 204. For instance, information related to the locations, shapes, dimensions, orientations and configurations of the imaged markers may be generated from the acquired images. Such information may be utilized, as indicated by decision block 206, to determine whether a correct device model is being utilized for the particular procedure being performed. In some aspects, a rigid body model, optionally including points of flexure, may be modeled using a limited number of degrees a freedom. If a determination is made that an incorrect model is utilized, the process 200 may be terminated.

At process block 208, a vector or line defining an orientation of the device in two or three-dimensions may be determined using identified locations for at least a first and a second marker associated with the device. As indicated by process block 212, multiple vectors may be obtained by aiming or orienting the device in multiple directions and repeating data acquisition for each direction to determine the multiple vectors or lines. As described, this step of orienting the pivoting guide may or may not require manipulation by an operator or clinician. When a condition is fulfilled at decision block 210, for instance, vectors for a desired number of pivoting guide orientations have been determined, a pivot point is then computed using the determined vectors, as indicated by process block 214.

Figure 4B:
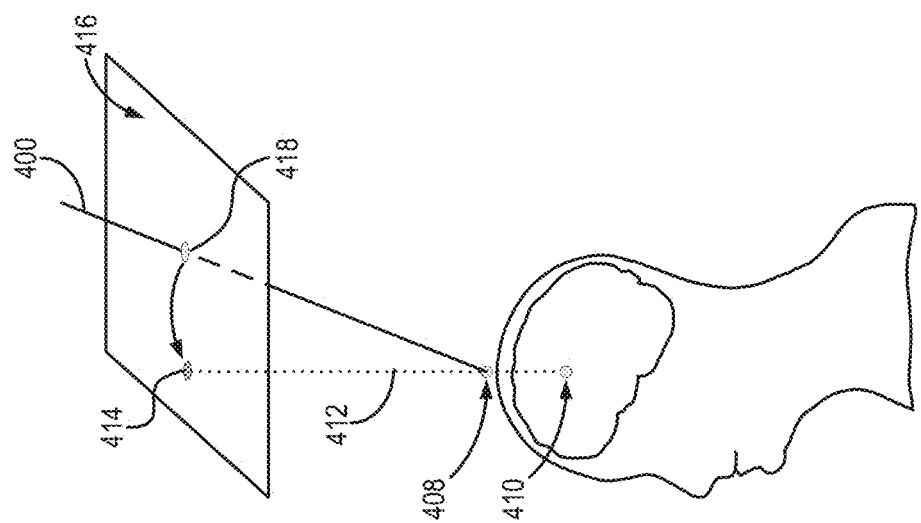
FIG. 4B is a schematic showing a method for controlling a pivoting guide orientation, in accordance with aspects of the present disclosure.
Figure 4A:
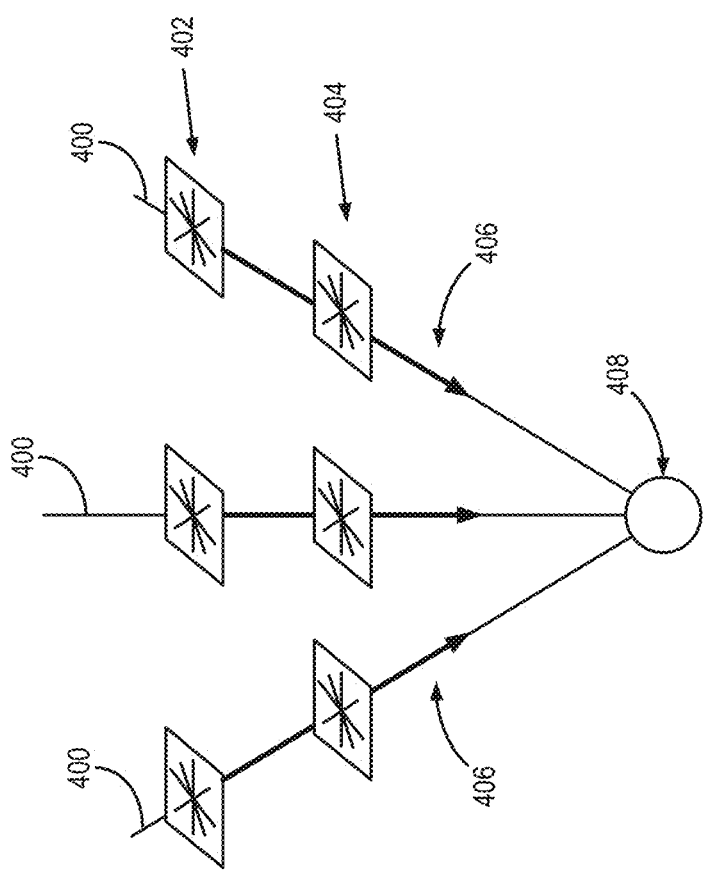
FIG. 4A is a schematic showing a method for determining a pivoting point for a pivoting guide, in accordance with aspects of the present disclosure.

The above steps may be visualized in the illustration of FIG. 4A. In the non-limiting example provided in FIG. 4A, a pivoting guide 400 is the device, such as described above with respect to FIG. 2. The pivoting guide 400 may be oriented in 2 or more distinct directions. Regardless of the particular orientation of the pivoting guide 400, a first location 402 and second location 404 along the pivoting guide 400 may be computationally measured. Although the pivoting guide 400 is depicted in FIG. 4A as a linear element, it may be appreciated that other shapes or configurations may also be possible for the pivoting guide 400. For instance, the pivoting guide 400 may include one or more points of flexure, as well as other features. Positions for the markers may then be identified using the acquired data, either autonomously, or semi-autonomously, and utilized to determine respective vectors 406, pointing generally to a common location or pivot point 408. In some aspects, the pivot point 408 may be obtained by computing an intersection of the determined vectors 406, for example, using a least squares algorithm.

Returning to FIG. 2, at process block 216, a trajectory for an interventional device can be determined using the identified pivot point and the selected target point and communicated in a report at process block 218. The report may serve as a guide to indicate a future arrangement of the interventional device within the subject's anatomy using the determined location or orientation. Alternatively, in the case that a device controller is utilized, as described with regard to FIG. 1, the report may be used by the device controller to move an interventional device or a device guide to the projected or future arrangement in the subject's anatomy.

For example, in the case of the pivoting guide 400 described above with respect to FIG. 4A, the pivoting guide 400 or another device guide may then be oriented along a direction substantially collinear to the projected trajectory, at process block 218. An interventional device, such as a trocar, or cannula, may then be positioned within the subject using the device controller 112, by way of the pivoting guide 400 or another device guide. In some aspects, at process block 218, images associated with one or more imaging planes may be acquired and analyzed. Specifically, multiple images from at least one imaging plane may be obtained in substantially real-time, for example, by performing a fast imaging sequence, such as a gradient recalled echo sequence, using an MRI system. In some implementations, an undersampled radial k-space sampling may be utilized, although it may be appreciated that other imaging approaches suitable for real-time imaging may also be utilized. In some aspects, images may be acquired at a rate of about five per second, although it may be appreciated that other frame rates may also be possible. By way of example, about 18 full projections, with 512 samples each and a field of view of about 20 cm may be utilized to produce about 5 frames a second. It may be appreciated that other imaging strategies may also be utilized.

As described, orienting the pivoting guide may be achieved via operator or clinician manipulation or may be automated. In either case, using the determined trajectory and images obtained at process block 218, a current position of the pivoting guide in at least one imaging plane, as well as its spatial relation to an aim position in the imaging plane, may be provided.

By way of example, FIG. 4B illustrates a trajectory 412 determined using the identified pivot point 408 and selected target point 410. The intersection of the trajectory 412 and an imaging plane 416 or 2D field of view produces an aim position 414 in relation to a current position 418 for the pivoting guide 400. An operator or clinician or an automated controller may then control the pivoting guide to control the distance between the current position 418 and the target position 414, or bring the current position 418 within sufficient distance of the target position 414. To achieve this, computed measurements, images, as well as other information, may be used to form a report. Such a report, provided in substantially real-time, for instance, can facilitate orienting the pivoting guide, or other device guide, along the direction substantially collinear to the determined trajectory by providing direct and intuitive feedback related to the current position and aim position of the pivoting guide, or other device guide, in a given field of view or imaging plane.

Figure 5:
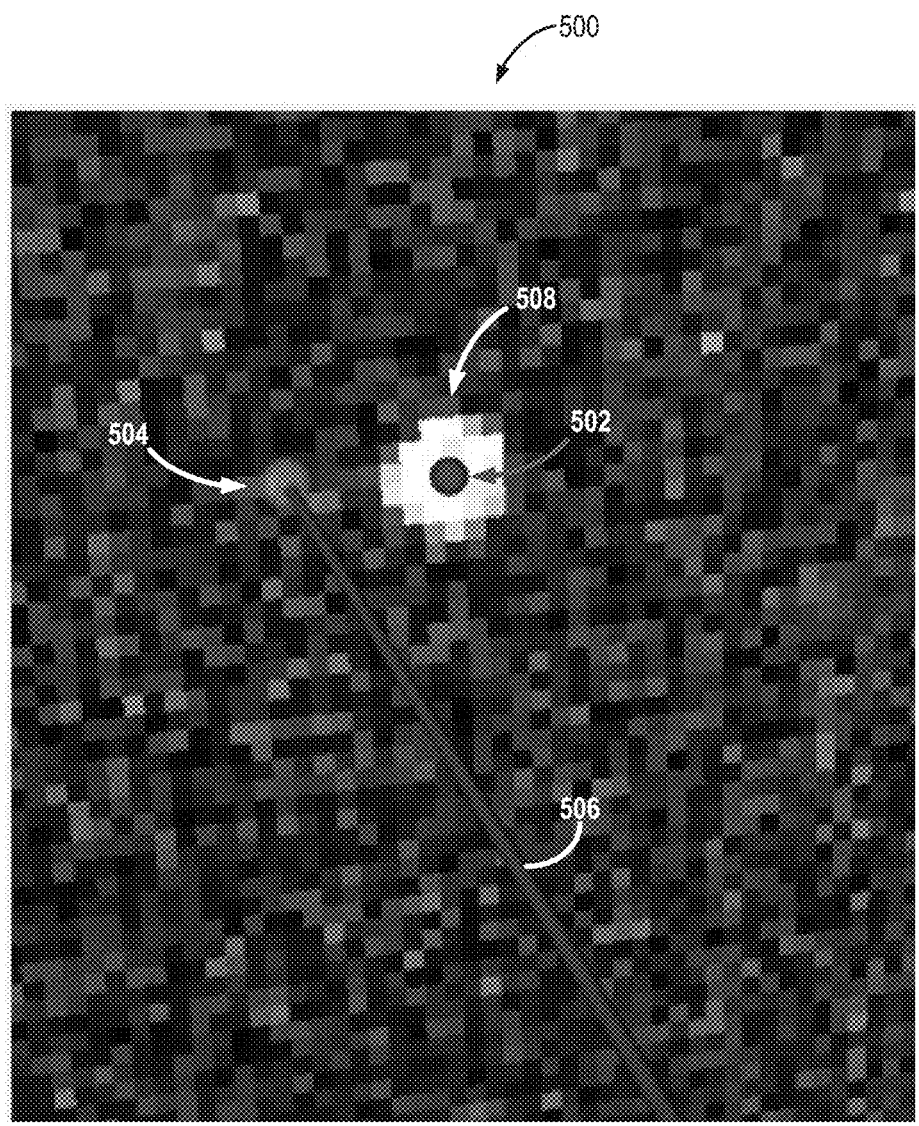
FIG. 5 is an example radial image illustrating a trocar's real-time position relative to a target trajectory.

By way of example, FIG. 5 shows an image 500 output that may be provided to an operator or clinician via a display, depicting a rendered trajectory and target relative to a current position of markers on the pivoting guide. In the illustrated image 500, which may form a part of the above-described report, the current point 502 and aim point 504 are illustrated, as is a projected future path 506 that would be followed if an interventional device were inserted upon bringing the current point 502 to the aim point 504. As shown in FIG. 5, the current point 504, computed using acquired MR data as described, is rendered as a 3D point that falls within an imaged cross section 508 of the pivoting guide, depicted in the image 500 as a circular region of high signal intensity in the otherwise noisy background. In some aspects, rendering the future path 506 as a 3D line allows an operator or clinician to evaluate which structures the interventional device would pass through on its way to a target anatomical structure. As can be seen the current position of the pivoting guide would result in the inserted interventional device not arriving at the target point. Thus, an operator or clinician (or, if automated, a controller) can use computed points from the data, and other information, as shown for example in the image 500 of FIG. 5, to make adjustments.

However, the image of FIG. 5 is but one example of the information that may be included in the report or used to determine a desired positioning of a device or device guide. For example, when intersecting an image plane a device or device guide can generate a cross-sectional shape that may depend on its position or orientation relative to the image plane. In the example illustrated in FIG. 4B, the current orientation of the device 400 relative to the image plane 416 is not orthogonal and, thus, the cross-section formed at position 418 by the device 400 is an oval having characteristics that indicate its distance from the target position 414. If moved to the target position 414, which in the illustrated example corresponds to the device 400 being oriented orthogonal to the image plane 416, the cross-section of the device 400 will tend toward a circular shape. This cross-sectional information can be used in addition to or instead of the positional information described above with respect to FIG. 5 to facilitate the desired positioning in real-time or near real-time.

In some aspects, an audio and/or visual signal may be provided to the operator or clinician at process block 218 when the orientation of the pivoting guide is substantially collinear to the determined or projected trajectory. In addition, the audio and/or visual signal may be configured to guide or indicate to the operator or clinician how to control or adjust the pivoting guide to achieve an orientation substantially collinear to the determined trajectory. For example, as described above, an image depicting a current and a target position for a pivoting guide, or another device guide, may be provided to the operator or clinician via a display. Alternatively, or additionally, an audio signal may be modulated in accordance with a difference between the current and target positions of the pivoting guide. Other information may also be provided.

Figure 6:
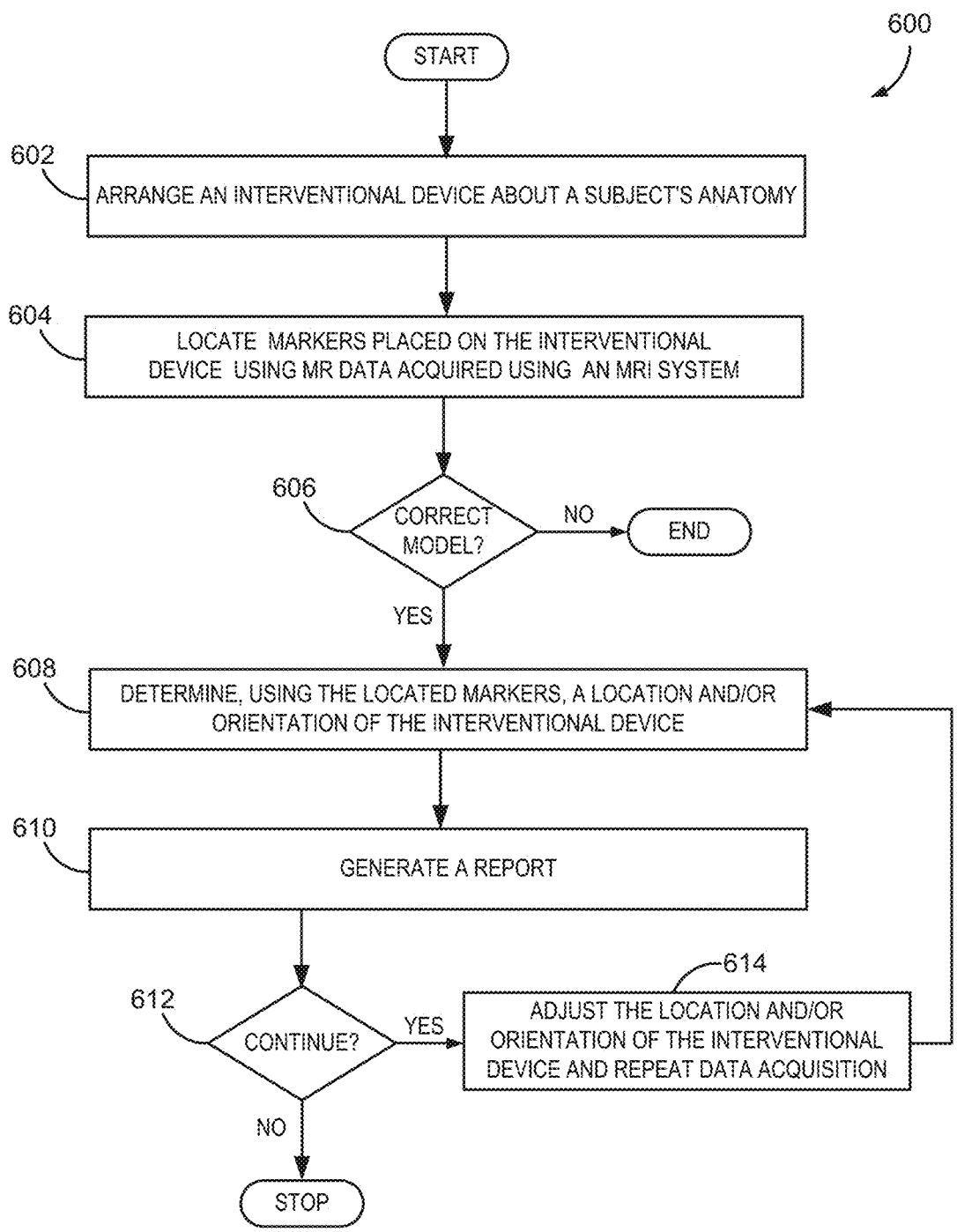
FIG. 6 is a flowchart setting forth steps of a process in accordance with aspects of the present disclosure.

Turning to FIG. 6, the steps of one particular example of a process 600 for controlling an interventional device during a medical procedure using computed guidance, in accordance with aspects of the present disclosure, are shown. By way of example, the medical procedure can be a biopsy procedure, such as a breast biopsy procedure. The process 600 may begin at process block 602 where an interventional device is arranged about a subject's anatomy, or prepared for insertion into a target tissue or structure of the subject's anatomy. In some aspects, an operator or clinician may determine a trajectory for the interventional device by selecting an entry point and target in the subject's anatomy using roadmap images, such as 3D MR images. Then, at process block 604, markers placed on the interventional device may be located using data acquired from one or more imaging planes, or 2D fields of view, using an imaging system as described with reference to FIG. 1.

Following a verification step at process block 606, which may include an analysis of markers and other features identified at process block 604 to determine whether a model for the interventional device utilized is correct, one or more locations of the device may be determined, as indicated by process block 608. In some aspects, intersection points of the interventional device with one or more imaging planes, or 2D fields of view, may be determined at process block 608. In some aspects, imaging planes may be configured to be substantially orthogonal to an insertion path or trajectory of the interventional device. An orientation of the interventional device may be computed using two or more such determined intersection points. In some aspects, the imaging planes may be substantially in-plane relative to at least a portion of the interventional device, such that an insertion depth of the device can be monitored. Additional information regarding the interventional device may also be obtained at process block 608, based on the number of degrees of freedom of the device. For example, one or more shapes, dimensions, angles, or cross sections of the interventional device may be determined by analyzing MR data or images generated therefrom.

Then at process block 610, a report may be generated. As described, the report may take any form, and can include audio and/or visual signals or indicators. In accordance with some aspects of the present disclosure, process blocks 608 and 610 may be repeated following a decision to continue at block 612 and adjustment of the location and/or orientation of the interventional device, as indicated by process block 614. As described, such adjustment may be performed manually by an operator or clinician. In that case, a real-time report may be provided at process block 610, providing guidance to the operator or clinician while performing the selected medical procedure.

In some applications, fully automated therapeutic procedures using computational guidance may be desirable, for example, via in-bore positioning systems or robotics for use with an MRI system. As such, redundant safety mechanism may be used to prevent errors, such as missing the lesion or puncturing the chest wall during a biopsy procedure, for example. As such process blocks 604-614 may be performed in an automated fashion to obtain information about and/or control the position and orientation of the interventional device, preferably in substantially real-time. In some aspects, if a measured alignment or depth is found to be outside of an appropriate range, a signal may be given to quickly halt the robotic system. In some implementations, input from an operator or clinician may be accepted, such as selection of a target point in a subject's anatomy. In addition, a report may be provided to the operator or clinician regarding the orientation and/or position of the interventional device.

Figure 7:
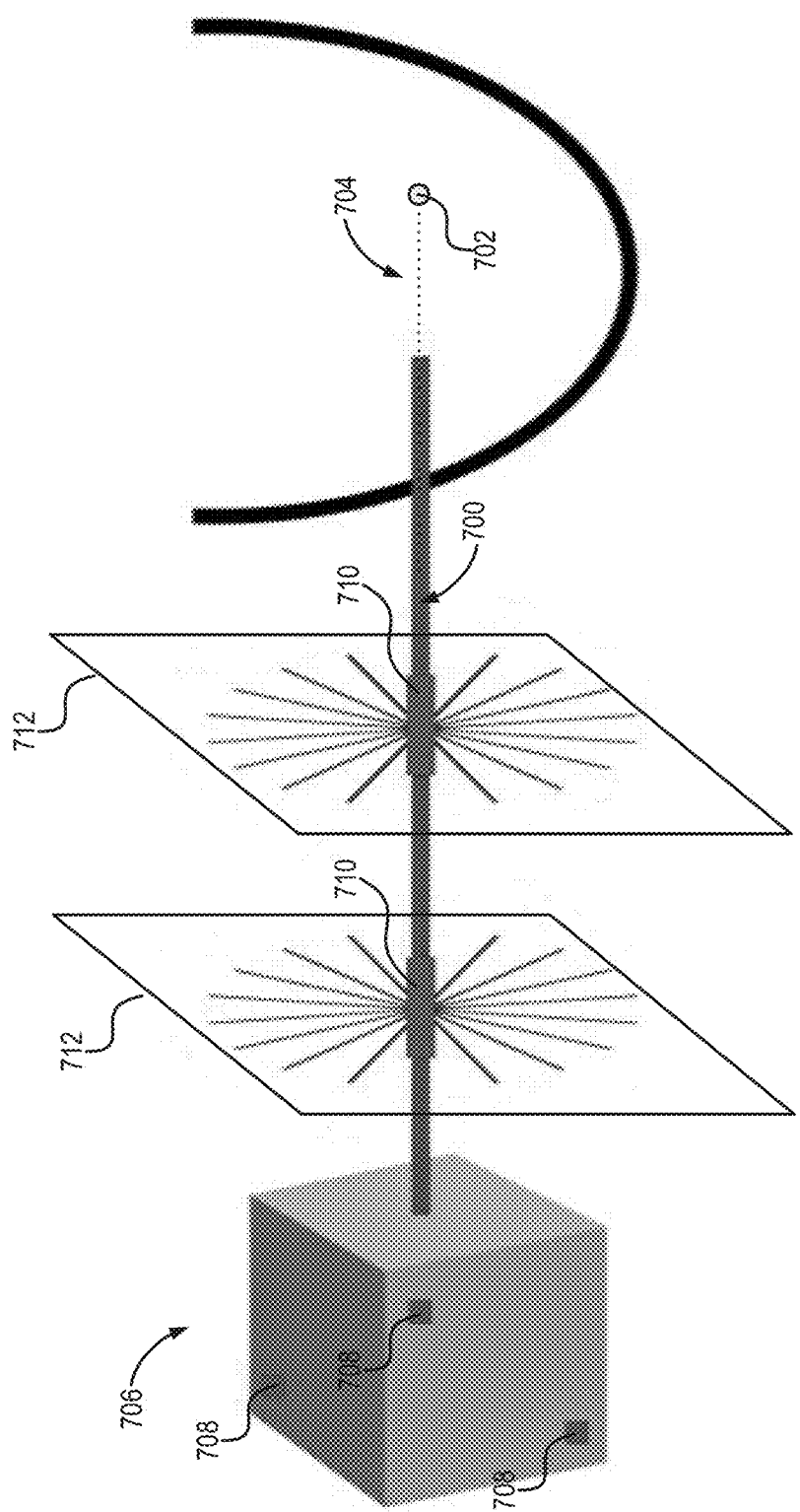
FIG. 7 is a schematic diagram showing a trocar robotically inserted into tissue, in accordance with aspects of the present disclosure.

By way of example, FIG. 7 shows a schematic diagram illustrating a trocar 700 robotically inserted into a target tissue 702. Using an operator or clinician selected device trajectory 704 and knowledge of a device controller or robotic system 706 position, its MR-visible platform fiducials 708, and its MR-visible device markers 710, rapid, real-time, reduced field of view computational measurement in selected planes 712 can periodically validate the robotic reference frame, trocar 700 orientation, and trocar 700 location. Specifically, the sparsity of MR signal generating sources on the robotic system 706 permits rapid, reduced FOV methods to be used to determine the platform's variable orientation. Similarly computational measurement of the MR-visible device markers 710, such as MR-visible fluid pockets or activated microcoils, on the MR-compatible trocar 700, which may be fashioned using an MR-compatible material such as a ceramic, for example, facilitate real-time feedback and adjustment.

A trocar orientation can be determined by performing two or more computational measurements, for example, with about 0.2 seconds per measurement, in two or more planes normal to the trajectory reported by the insertion robot. An insertion depth can be determined via a fully sampled 2D Cartesian real-time acquisition with the trocar in-plane, as shown in the example of FIG. 8. Rapid acquisition of images from a 2D radial sequence was demonstrated with only about 18 full projections (5 ms TR) with in-plane resolution of $0.39 \times 0.39$ mm$^2$, although it may be appreciated that other imaging strategies may also be utilized. Including both data acquisition and processing time, a measurement of fiducial location could be completed in 200 ms, thus permitting rapid validation of the robotic geometry frame and the trocar orientation it creates. Real-time MR imaging control was achieved with the RTHawk development platform (HeartVista, Menlo Park, Calif.) interfacing with a GE Healthcare MR750 3T scanner (Waukesha, Wis.). A visualization software, Vurtigo, was modified to render 3D lines to indicate the planned trajectory. A trocar trajectory, which may be derived from the insertion robot's spatial encoders, may be rendered as a 3D line viewable along with the rapid 2D image and computational measurements, similar to the example of FIG. 5, providing quick verification as to whether the device is on the proper course. As may be appreciated, the above approach can be used to provide a rapid, redundant approach to validate the location and/or orientation of MR devices during an invasive medical procedure, such as a breast biopsy procedure, for example.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for controlling an interventional device using magnetic resonance imaging ("MRI") guidance, the method comprising:
   a) generating, using an MRI system, magnetic resonance ("MR") data of an interventional device arranged about a subject's anatomy and having a first marker and a second marker placed on the interventional device, wherein the first marker and the second marker are separated in at least one axial direction of the interventional device;

b) determining locations for the first marker and the second marker relative to the subject's anatomy using the MR data by determining k-space readout locations for the first marker and the second marker, and generating a convolution in image space from the k-space readout locations using an inverse Fourier transform;

c) computing, using a processor, a vector using the determined locations;

d) determining at least one of a location or an orientation for the interventional device relative to the subject's anatomy using the computed vector;

e) projecting a future arrangement of the interventional device within the subject's anatomy using the determined location or orientation;

f) generating a report indicating the future arrangement of the interventional device relative to the location or orientation;

wherein determining locations for the first marker and the second marker includes performing a 1D inverse Fourier transform of the k-space readout locations; and wherein the convolution includes convolving a rectangular function with 1D data in image space from the 1D inverse Fourier transformation.

2. The method of claim 1, wherein step a) includes acquiring two-dimensional image data using the MRI system.

3. The method of claim 2, wherein acquisition of the two-dimensional image data includes performing a radial projection sampling sequence.

4. The method of claim 1, wherein the method further comprises analyzing the MR data associated with at least one of the first marker and the second marker to determine marker information that includes at least one of a location, a shape, a dimension, an orientation, or combinations thereof.

5. The method of claim 4, wherein the method further comprises using the marker information to verify a model of the interventional device.

6. The method of claim 1, wherein the method further comprises repeating steps a) through d) and generating a report indicative of the determined location or orientation of the interventional device in 200 ms.

7. The method of claim 1, wherein determining locations for the first marker and the second marker includes using readout datasets without reconstructing images of the first marker and the second marker.

8. A method for controlling an interventional device using magnetic resonance imaging ("MRI") guidance, the method comprising:

a) generating, using an MRI system, magnetic resonance ("MR") data of an interventional device arranged about a subject's anatomy and having a first marker and a second marker placed on the interventional device, wherein the first marker and the second marker are separated in at least one axial direction of the interventional device;

b) determining locations for the first marker and the second marker relative to the subject's anatomy using the MR data by determining k-space readout locations for the first marker and the second marker, and generating a convolution in image space from the k-space readout locations using an inverse Fourier transform;

c) computing, using a processor, a vector using the determined locations;

d) determining at least one of a location or an orientation for the interventional device relative to the subject's anatomy using the computed vector;

e) projecting a future arrangement of the interventional device within the subject's anatomy using the determined location or orientation;

f) generating a report indicating the future arrangement of the interventional device relative to the location or orientation; and wherein generating the convolution in image space includes multiplying the k-space readout locations by a Fast Fourier Transform ("FFT") of a rectangular function, and performing a 1D inverse FFT of the multiplied k-space readout locations.

9. The method of claim 8, wherein step a) includes acquiring two-dimensional image data using the MRI system.

10. The method of claim 9, wherein acquisition of the two-dimensional image data includes performing a radial projection sampling sequence.

11. The method of claim 8, wherein the method further comprises analyzing the MR data associated with at least one of the first marker and the second marker to determine marker information that includes at least one of a location, a shape, a dimension, an orientation, or combinations thereof.

12. The method of claim 11, wherein the method further comprises using the marker information to verify a model of the interventional device.

13. The method of claim 8, wherein the method further comprises repeating steps a) through d) and generating a report indicative of the determined location or orientation of the interventional device in 200 ms.

14. The method of claim 8, wherein determining locations for the first marker and the second marker includes using readout datasets without reconstructing images of the first marker and the second marker.

* * * * *

UNITED STATES PATENT AND TRADEMARK OFFICE
CERTIFICATE OF CORRECTION

PATENT NO. : 11,269,028 B2
APPLICATION NO. : 14/725847
DATED : March 8, 2022
INVENTOR(S) : Miles E. Olsen et al.

It is certified that error appears in the above-identified patent and that said Letters Patent is hereby corrected as shown below:

In the Specification

Column 1, Line 26, "("MW")" should be --("MR")--.

Column 4, Line 39, "("MW")" should be --("MR")--.

Signed and Sealed this
Twenty-fourth Day of May, 2022

Katherine Kelly Vidal
*Director of the United States Patent and Trademark Office*